United States Patent [19]
Abou-Gharbia et al.

[11] Patent Number: 4,710,572
[45] Date of Patent: Dec. 1, 1987

[54] HISTAMINE $H_1$ ANTAGONISTS

[75] Inventors: Magid A. Abou-Gharbia; Susan T. Nielsen, both of Wilmington, Del.

[73] Assignee: American Home Products Corporation, New York, N.Y.

[21] Appl. No.: 892,159

[22] Filed: Jul. 30, 1986

[51] Int. Cl.$^4$ .................... C07D 473/08; A61K 31/52
[52] U.S. Cl. .................................. 544/267; 514/265; 544/269
[58] Field of Search ...................... 544/277, 276, 267; 514/265

[56] References Cited

U.S. PATENT DOCUMENTS 4,426,383  1/1984  Sugimoto et al. .................. 424/253

FOREIGN PATENT DOCUMENTS 894597  1/1983  Belgium .

Primary Examiner—Nicholas S. Rizzo
Attorney, Agent, or Firm—Richard K. Jackson

[57] ABSTRACT

N-Theophyllin-7-ylalkylene-$N^1$-(bis-p-fluorophenyl)-methyl-piperazine derivatives as histamine $H_1$-antagonists.

1 Claim, No Drawings

HISTAMINE H₁ ANTAGONISTS

BACKGROUND OF THE INVENTION

U.S. Pat. No. 4,426,383 discloses a group of theophylline derivatives which serve as vasodilators useful for increasing blood flow in the treatment of circulatory insufficiency. The compounds are also disclosed to control blood platelet aggregation, act on the central nervous system (psychic energizers), provide antihistamine, analgesic, anti-asthmatic and hypotensive actions.

DESCRIPTION OF THE INVENTION

In accordance with this invention there is provided a group of histamine $H_1$-antagonists of the formula:

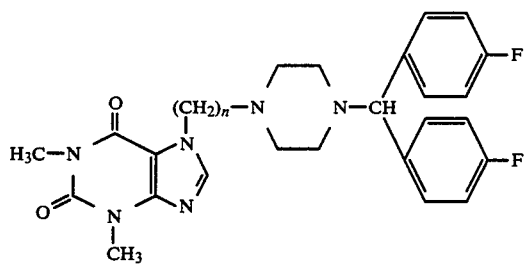

where n is one of the integers from 2 to 10, preferably from 2 to 4, or a pharmaceutically acceptable salt thereof, which exhibit a weak neuroleptic potential, no antipsychotic activity, and are without sedative side effects. As $H_1$-antagonists, the compounds of this invention are, more potent than terfenadine, 100 percent effective in inhibition of histamine-induced death in the guinea pig at 5 mg/kg dosage, block histamine induced wheal or edema formation and reverse histamine induced bronchopulmonary parameters in the anesthetized guinea pig. All of which catagorize the compounds as having good potency and duration of activity with a non-sedating, clean activity profile.

The compounds of this invention are prepared by methods known in the art, as follows:

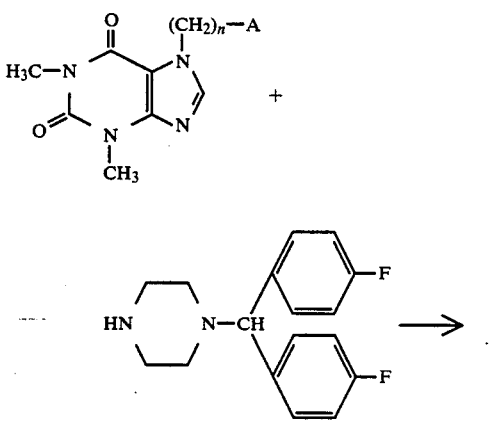

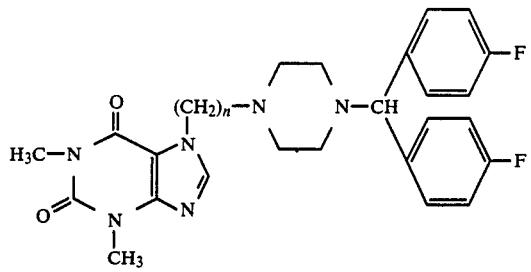

where A is a good leaving group such as a halogen or the tosyloxy group. The production of the depicted theophylline reactant is achieved by reaction of a dihaloalkane Hal-$(CH_2)_n$Hal with theophylline in the presence of sodium hydride. The alkylation of bis(4-fluorophenyl)methylpiperazine goes smoothly in the presence of an acid binding agent such as triethylamine in dimethylformamide as the reaction solvent.

The pharmaceutically acceptable salt of the anti-histaminic agents of this invention are prepared by conventional means with inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention were established to be histamine $H_1$-antagonists by subjecting 7-[3-[4-bis(4-fluorophenyl)methyl]-1-piperazinyl]propyl-3,7-dihydro-1,3-dimethyl-1$\underline{H}$-purine-2,6-dione, a representative member of the genus of compounds, to the following standard test procedures for $H_1$-blocking activity:

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-7}$M. The response was noted as grams tension. Test drug was added, in the presence of histamine, to each bath to a final concentration of $1 \times 10^{-6}$M. The change in grams tension was noted and the percent reduction in grams tension calculated.

The results obtained in accordance with this procedure established that the compound exemplified, infra, exhibits a potent, competitive antagonist action against the histamine-induced contractile response in the isolated guinea pig ileum.

Subsequently, additional characterization of the compound herein exemplified was carried out in which complete histamine dose response curves were constructed first in the absence of test drug and then repeated in the presence of test drug at a specified concentration. A single experiment of this type allowed calculation of a $pK_B$ value from the rightward shift induced by the drug in the histaminic dose response curve, while three such experiments (at three different drug concentrations) allowed calculation of a $pA_2$ value. A $pA_2$ value of 8.2 was established for the compound exemplified herein, all shifts being parallel rightward shifts with no decrease in the maximum response, demonstrating competitive displacement of antagonist by histamine from the receptor sites. By comparison, terfenadine was competitive at the lowest concentration tested ($pK_B = 7.5$) and non-competitive at higher doses, indicating that the representative compound of this invention is about five times as potent as terfenadine, in vitro.

The compound exemplified herein, after a one hour pretreatment period, inhibited histamine-induced deaths in guinea pigs over the range of 1–5 mg/kg, with 100 percent effectiveness at the latter dose. At 18 hours post drug treatment the test compound retained 40 percent effectiveness at 10 mg/kg. The test compound demonstrated good in vivo potency, a short latency period in terms of onset of action and a reasonably long duration of action.

In further studies, the exemplified compound was shown to block histamine-induced wheal formation in guinea pig skin, showing effectiveness over a dose range of 0.84–2.1 mg/kg when evaluated after a one hour pretreatment period. Maximum suppression of wheal formation was observed at the highest dose. After an 18 hour pretreatment period, the compound still retained maximal effectiveness at a dose of 1.7 mg/kg. The reversal of histamine-induced changes in bronchopulmonary parameters in the anesthetized guinea pig and inhibition of histamine-induced paw edema formation were also observed activities of the compound under standard test procedures.

In addition to the excellent potency as an $H_1$-antagonist, the representative compound of this invention demonstrated inhibition (43 percent at 1 $\mu$M) of limbic $D_2$ dopamine receptor binding (indicative of very weak neuroleptic activity) when tested in a manner similar to that of Fields et al. Brain Res., 136, 578–584 (1977). In studies of conditioned avoidance (shelf-jump) following the procedure of Herman et al., Comm. in Psychopharmacology, 3, 165–171 (1979) the compound was inactive at 40 mg/kg, indicating a low potential for antipsychotic activity. In studies of confinement motor activity, Tedeschi et al. J. Pharmaceutical Sciences, 53, 1046–1050 (1964), no sedative effect was achieved at 5 and 10 mg/kg i.p. Similarly in a modified Geller-Seifter experimentally-induced conflict test (Geller et al., Psychopharmacologia 1, 482–492 (1960)), the representative compound of this invention produced mild stimulation which confirms its lack of sedative effects.

The compound exemplified herein, which is a representative of the other compounds claimed, was directly compared with the closest structural analogues found in the prior art reference U.S. Pat. No. 4,426,383 (-383), namely 7-[4-[4-(4',4''-dichlorodiphenylmethyl)piperazinyl-(1)]-n-butyl]theophylline (a dichloro analogue of the claimed compounds and 7-[3-[4-p-chlorobenzhydrylpiperazinyl-(1)]-n-propyl]-theophylline (a monochloro analogue of the claimed compounds), according to the following procedure: Male Hartley guinea pigs weighing 250–300 g were killed by cervical dislocation. A section of terminal ileum was removed and suspended in aerated 37° C. Tyrodes solution. After one hour equilibration period, histamine was added to each tissue bath to a final concentration of $1 \times 10^{-6}$M. When the contractions levelled off and had been recorded, the drug was added and the resulting change in tension recorded. Tissues were washed several times before repeating the procedure for the next concentration. A different set of 4 tissues was used for each drug.

| Drug Conc. (M) | Drugs vs. Histamine at $1 \times 10^{-6}$ M Reduction in Grams Tension | | |
|---|---|---|---|
| | -383 Monochloro compound | -383 Dichloro compound | Difluoro compound |
| $1 \times 10^{-8}$ | 7 | 16 | 24 |
| $1 \times 10^{-7}$ | 29 | 14 | 71 |
| $1 \times 10^{-6}$ | 69 | 54 | 98 |

The results of this study demonstrate the marked superiority in the potency of the compounds claimed. The IC$_{50}$'s (inhibitory concentration$_{50}$) calculated from these data were $3.8 \times 10^{-8}$M for the difluoro compound of this invention, $3.7 \times 10^{-7}$M for the reference monochloro compound, and $7.9 \times 10^{-7}$M for the reference dichloro compound. The difluoro compound of this invention is therefore, 10 times as potent as the -383 monochloro compound and about 21 times as potent as the -383 dichloro compound.

The pharmacological results obtained characterize the compounds of this invention as $H_1$-receptor antagonists useful in the treatment of conditions such as asthma, hay fever, allergic rhinitis, atopic dermatitis and eczema. As such, they may be administered topically or systemically. Topical administration is advantageously achieved to the skin via creams, ointments or lotions, or via aerosol introduction into the respiratory tract. Systemic administration may be orally, parenterally or rectally. In each instance, conventional formulations amenable to use in the desired administration route is appropriate. Hence, tablets and capsules may be prepared for oral administration, suppositories for rectal administration and isotonic aqueous solutions for intravenous, subcutaneous or intramuscular injection.

As is conventional in the use of antihistaminic agents, the appropriate dosage is determined on a subjective basis by initial administration of small amounts, ca. 1–15 mg. followed by increasing quantities up to about 400 mg. by topical, oral, or rectal routes and about 200 mg. intravenous, until the desired symptomatic relief is obtained. The dosage is personalized in this manner for each patient, based upon size, age, type of discomfort, degree of disability etc. by the physician.

The following example is presented to illustrate the preparation of a representative compound of this invention.

7-[3-[4-bis(4-fluorophenyl)methyl]-1-piperazinyl]propyl-3,7-dihydro-1,3-dimethyl-1H-purine-2,6-dione A solution of 0.45 g (0.019 mol) of sodium hydride (prepared from 0.76 g of 60% sodium hydride in mineral oil by pentane washing) in 50 mL of dimethylformamide is treated portionwise with 3.4 g (0.01 mol) of theophylline.

The resulting solution is added dropwise to a stirred solution of 15 g (0.07 mol) of 1,3-dibromopropane in 40 mL of dimethylformamide. The reaction mixture is stirred overnight and the solvent is removed under vacuum and the residue partitioned between methylene chloride and water.

The combined methylene chloride extracts are washed with brine and dried over anhydrous $Na_2SO_4$. 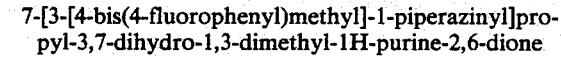
Filtration and removal of the solvent in vacuo affords 4 g (74% yield) of 7-(3-bromopropyl)-3,7-dihydro-1,3-dimethyl-1H-purine-2,6-dione as a waxy solid.

The title compound was prepared by adding to a stirred solution of 3.5 g (0.012 mol) of 7-(3-bromopropyl)-3,7-dihydro-1,3-dimethyl-1H-purine-2,6-dione in 50 mL of dimethylformamide, 4 mL of triethylamine and 3.0 g (0.01 mol) of 1-[bis(4-fluorophenyl)methyl]-piperazine. The reaction mixture is stirred overnight and the solvent is removed under reduced pressure and then is partitioned between water and methylene chloride. The methylene chloride extracts are combined, dried over anhydrous $Na_2SO_4$, filtered and rotoevaporated to give crude free base. Preparative HPLC (silica gel, ethylacetate, methylene chloride, 9:1) followed by evaporation of the appropriate fractions (TLC $R_f=0.2$), treatment with ethanolic hydrogen chloride and recrystallization from ethanol gives the titled compound as a dihydrochloride, sesquihydrate; mp 240°–242° C.

Analysis for: $C_{27}H_{30}F_2N_6O_2 \cdot 2HCl \cdot 1\frac{1}{2}H_2O$. Calculated: C, 53.28; H, 5.75; N, 13.81. Found: C, 53.14; H, 5.43; N, 13.44.

What is claimed is:

1. The compound which is 7-[3-[4-bis(4-fluorophenyl)methyl]-1-piperazinyl]propyl-3,7-dihydro-1,3-dimethyl-1H-purine-2,6-dione or a pharmaceutically acceptable salt thereof.

* * * * *